United States Patent [19]

Wassen et al.

[11] 4,133,810

[45] Jan. 9, 1979

[54] PROCESS FOR THE RECOVERY OF ε-CAPROLACTAM FROM A REACTION MIXTURE OF ε-CAPROLACTAM AND SULFURIC ACID

[75] Inventors: Willem J. Wassen; Rudolf L. Zwart, both of Geleen, Netherlands

[73] Assignee: Stamicarbon, B.V., Geleen, Netherlands

[21] Appl. No.: 871,005

[22] Filed: Jan. 20, 1978

[30] Foreign Application Priority Data

Jan. 28, 1977 [NL] Netherlands .......................... 7700882

[51] Int. Cl.$^2$ ............................................. C07D 201/16
[52] U.S. Cl. ........................... 260/239.3 A; 423/541 A
[58] Field of Search .................................. 260/239.3 A

[56] References Cited

U.S. PATENT DOCUMENTS

| | | | |
|---|---|---|---|
| 2,993,889 | 7/1961 | Muytjens et al. | 260/239.3 A |
| 3,336,298 | 8/1967 | De Rooij | 260/239.3 A |
| 3,850,910 | 10/1972 | Goettsh et al. | 260/239.3 A |
| 3,852,223 | 12/1974 | De Rooij | 260/239.3 A |
| 3,859,278 | 1/1975 | De Rooij et al. | 260/239.3 A |
| 3,879,380 | 4/1975 | De Rooij et al. | 260/239.3 A |
| 4,021,422 | 5/1977 | De Rooij et al. | 260/239.3 A |
| 4,049,646 | 9/1977 | Furkert | 260/239.3 A |
| 4,054,562 | 10/1977 | Furkert | 260/239.3 A |
| 4,081,442 | 3/1978 | Wassen et al. | 260/239.3 A |

FOREIGN PATENT DOCUMENTS

| | | | |
|---|---|---|---|
| 7607047 | 6/1976 | Netherlands | 260/239.3 A |
| 7601061 | 8/1977 | Netherlands | 260/239.3 A |

*Primary Examiner*—Henry R. Jiles
*Assistant Examiner*—Robert T. Bond
*Attorney, Agent, or Firm*—Cushman, Darby & Cushman

[57] ABSTRACT

An improvement of processes for the recovery of ε-caprolactam wherein a neutralized sulfuric acid is subjected to thermal decomposition, forming a gaseous mixture of ammonia and sulfur dioxide which is thereafter converted to an aqueous solution of ammonium sulfite and/or ammonium hydrogen sulfite which is then used for neutralization of the reaction mixture of lactam and sulfuric acid.

1 Claim, 2 Drawing Figures

PROCESS FOR THE RECOVERY OF ε-CAPROLACTAM FROM A REACTION MIXTURE OF ε-CAPROLACTAM AND SULFURIC ACID

The invention relates to a process for the recovery of ε-caprolactam from a reaction mixture of ε-caprolactam and sulfuric acid, as obtained, e.g., in the Beckmann rearrangement of cyclohexanone oxime, using sulfuric acid, oleum or sulfur trioxide, or in the preparation of caprolactam by reaction of cyclohexane carboxylic acid with a nitrosating agent in the presence of sulfuric acid.

BACKGROUND OF THE INVENTION

In processes such as just mentioned, the lactam can be recovered from the resulting reaction mixture of lactam and sulfuric acid in a known way (see, e.g., U.S. Pat. No. 2,993,889) by neutralizing the sulfuric acid in the reaction mixture by means of ammonia water, thus forming ammonium sulfate, after which the lactam can be separated from the resulting ammonium sulfate. This method has, however, the disadvantage that a large amount of ammonium sulfate is obtained as a by-product, which does not always find a ready market.

According to U.S. Pat. No. 3,336,298, this disadvantage can be obviated by omitting the aforesaid neutralization of the sulfuric acid in the reaction mixture, and, instead, converting the sulfuric acid into ammonium hydrogen sulfate by the addition of ammonium sulfate, and then separating the lactam from the ammonium hydrogen sulfate by extraction. The remaining by-product will then be a concentrated aqueous solution of ammonium hydrogen sulfate, which can be commercially used, e.g., in the decomposition of phosphate rock. While it is true that no ammonium sulfate is obtained as a by-product in this last-mentioned reprocessing method, the recovery of the desired lactam is still always coupled with the preparation of another product in a large quantity.

A method for the recovery of the lactam without the formation of by-products has been described in U.S. Pat. No. 3,852,272. In this method, the sulfuric acid is only partially neutralized with ammonia water and, after extraction of the lactam from the partially neutralized mixture, an aqueous solution containing ammonium hydrogen sulfate remains which is then subjected to a decomposition treatment to form sulfur dioxide. This sulfur dioxide is then used to make the sulfuric acid needed for the formation of the reaction mixture of lactam and sulfuric acid. A disadvantage of this method is, however, the loss of ammonia in the decomposition of ammonium hydrogen sulfate, since the ammonia in the ammonium hydrogen sulfate is fully burnt to nitrogen and water.

U.S. Pat. No. 3,879,380 also describes a method for the recovery of lactam in which no by-products are obtained, but in which no ammonia is burnt. In this method, the sulfuric acid is partially neutralized, i.e., to form an ammonium-hydrogen-sulfate melt, after which ammonia and sulfur trioxide are recovered separately from this melt by means of a suitable metal oxide, such as, e.g., zinc oxide. However, the recovery of ammonia and sulfur trioxide in this way is very expensive.

To improve these known processes, it has already been proposed (see non-prepublished Netherlands Patent Application No. 7,601,061, the disclosure of which is incorporated herein by reference), to decompose thermally the ammonium salt obtained in the complete or partial neutralization of the sulfuric acid so that a gaseous mixture containing ammonia and sulfur dioxide is formed. This gaseous mixture is then brought into contact with the reaction mixture of lactam and sulfuric acid. The ammonia will then be bound to the sulfuric acid, while a sulfur dioxide-containing gas is discharged. Netherlands non-prepublished application No. 7,601,061 was published Aug. 5, 1977 and corresponds to U.S. Pat. No. 4,081,442 issued Mar. 28, 1978.

According to still another proposal for improving the known processes (see non-prepublished Netherlands Patent Application No. 7,607,047, the disclosure of which is incorporated herein by reference), part of the ammonium hydrogen sulfate obtained in the partial neutralization of the reaction mixture of lactam and sulfuric acid is subjected to thermal decomposition, to form a gaseous mixture containing ammonia and sulfur dioxide, and this gaseous mixture is brought into contact with the remaining part of said ammonium hydrogen sulfate, whereby ammonia is bound and a sulfur dioxide-containing gas is discharged. The ammonium sulfate thus formed with the bound ammonia is then used for the partial neutralization of the reaction mixture of lactam and sulfuric acid. Netherlands non-prepublished application No. 7,607,047 was published Dec. 30, 1977 and corresponds in turn to U.S. application Ser. No. 810,568 filed June 27, 1977.

The sulfur dioxide gas thus obtained in the aforesaid proposed improvements can be in turn converted in sulphuric acid, oleum or sulfur trioxide to be used for instance in the rearrangement of cyclohexanone oxime to caprolactam.

It has now been found that the resulting sulfur dioxide-containing gas as such, is less than entirely suitable for the catalytic oxidation to sulfur trioxide. This is because of the reducing agent that has to be present in said thermal decomposition, e.g., the combustion products of oil or natural gas, so that the sulfur dioxide concentration is rather dilute in the resulting gas. Moreover, this gas contains compounds that have an adverse effect on the catalyst used for the oxidation of sulfur dioxide to sulfur trioxide.

It is therefore the essential object of the present invention to provide a process whereby a gas containing sulfur dioxide can be obtained that is more suitable for the catalytic conversion thereof to sulfur trioxide.

DESCRIPTION OF THE INVENTION

In the process according to this invention, for the recovery of ε-caprolactam from a reaction mixture of ε-caprolactam and sulfuric acid, and in which the sulfuric acid, after complete or partial neutralization with simultaneous formation of an ammonium salt, is separated from the lactam, and in which an organic solvent is used to form a solution of lactam in the organic solvent from which the lactam is recovered, the improvement is provided wherein all or part of the completely or partially neutralized sulfuric acid is subjected to thermal decomposition to form a gaseous mixture containing ammonia and sulfur dioxide, and this gaseous mixture is then brought into contact with water in an absorption device to form an aqueous solution containing ammonium sulfite and/or ammonium hydrogen sulfite. This aqueous solution, either as such or after being mixed with partially neutralized sulfuric acid that has not been subjected to the thermal decomposition, is then used for the neutralization of the reaction mixture of lactam and sulfuric acid, while the sulfur dioxide formed in this neutralization, and/or in said mixing, is discharged and used for oxidation to sulfur trioxide.

The resulting sulfur dioxide-containing gas is now hardly diluted with other gases and is advantageously very suitable for catalytic oxidation into sulfur trioxide.

The ammonium salts that can be formed in the complete or partial neutralization of the reaction mixture of lactam and sulfuric acid are ammonium sulfate, ammonium hydrogen sulfate, and tri-ammonium hydrogen sulfate (an equimolar compound of ammonium sulfate and ammonium hydrogen sulfate). If the total amount of sulfuric acid is converted into ammonium sulfate, it is called complete neutralization. In all other cases of neutralization, i.e., whenever less than 2 moles of $NH_4$ ions per mole of $SO_4$ ions are contained in the neutralized mixture, the neutralization is called partial. In partial neutralization, the ratio between the reactants is usually so chosen that the resulting neutralized mixture of lactam contains between about 0.7 and about 1.4 moles of $NH_4$ ions per mole of $SO_4$ ions.

The ammonium salts of sulfuric acid can then be decomposed into ammonia and sulfur dioxide in various known ways. For instance, the salt may be made to react with a reducing agent, such as sulfur and carbon monoxide, at a temperature of between about 150 and 400° C. (see U.S. Pat. No. 3,810,968). It is also possible to use carbon as the reducing agent at a temperature of about 370° to 390° C. (see U.S. Pat. No. 3,275,407). Alternatively, the combustion products of an oil or gas burner may be used at a temperature of 400°–600° C. (see British Patent specification No. 1,014,945).

The absorption of the gaseous mixture obtained in the thermal decomposition in water can very well be effected in a plate column through which water is pumped in countercurrent relation to the gaseous mixture. Also, other methods that are known in themselves may be used for this absorption. If the aqueous solution that is obtained from such absorption, and which contains ammonium sulfite and/or ammonium hydrogen sulfite is now brought in contact with the lactam/sulfuric acid reaction mixture, gaseous sulfur dioxide will then be formed which can be used for the preparation of sulfur trioxide. If the aqueous solution obtained from the absorption is first mixed with partially neutralized sulfuric acid that has not been subjected to thermal decomposition, and the resulting mixture is then brought in contact with the lactam/sulfuric acid reaction mixture, sulfur dioxide is formed in said mixing, which can be discharged as a gas and which can then also be used for the preparation of sulfur trioxide.

The ammonium salt to be thermally decomposed in the process according to this invention may also, if so desired, be so treated together with ammonium salt obtained in another process, e.g., the ammonium sulfate obtained from the so-called Raschig synthesis for the preparation of hydroxyl ammonium sulfate from ammonium nitrite (see, e.g., U.S. Pat. No. 2,785,954) or from the conversion of the hydroxyl ammonium sulfate into cyclohexanone oxime by means of cyclohexanone. Part of the aqueous solution containing the ammonium sulfite and/or ammonium hydrogen sulfite, and which is obtained in the absorption of the gaseous mixture containing ammonia and sulfur dioxide from the thermal decomposition, may also be used for other purposes, e.g., the preparation of hydroxyl ammonium sulfate by said Raschig synthesis.

The invention will now be further explained with reference to the accompanying drawings.

DESCRIPTION OF THE DRAWINGS

In FIG. 1, A denotes a rearrangement reactor, B a neutralization unit, C an extraction unit for extracting the lactam formed, D an apparatus for evaporation and for the decomposition of ammonium hydrogen sulfate and/or ammonium sulfate, E an installation for preparing sulfuric acid or oleum (in which sulfur dioxide is oxidised to sulfur trioxide) and F an absorption unit for the absorption in water of the gas containing $NH_3$ and $SO_2$.

Figure 1:
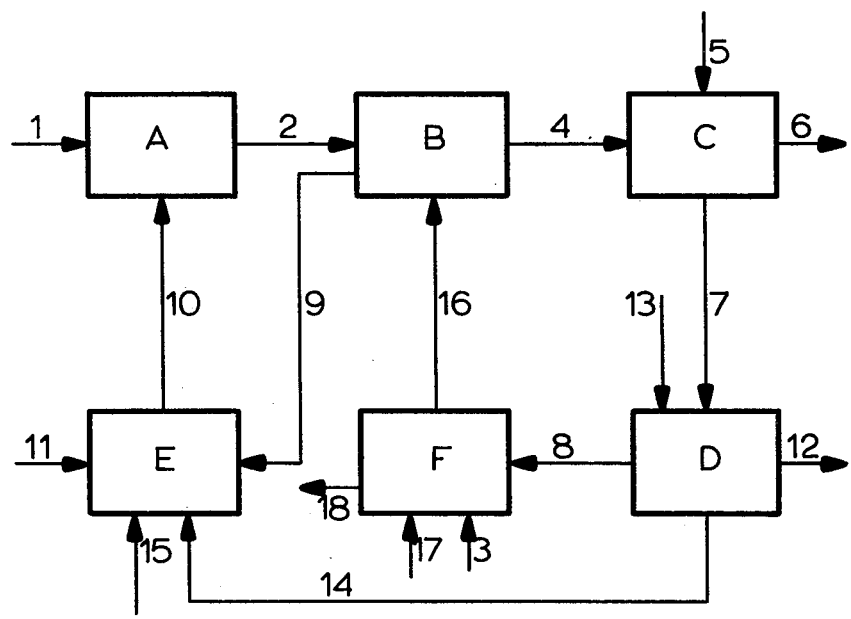
FIG. 1 schematically illustrates an installation for preparing ε-caprolactam in which the rearrangement reaction mixture is neutralized to ammonium hydrogen sulfate.

Thus, cyclohexanone oxime is passed through conduit 1 into rearrangement reactor A, to which oleum or sulphuric acid is also fed through conduit 10. The resulting reaction mixture of lactam and sulfuric acid flows through conduit 2 to neutralization unit B, to which through conduit 16 there is also fed the aqueous solution formed by the absorption in water, in absorption unit F, of the gaseous mixture of ammonia and sulfur dioxide obtained from the decomposition of ammonium hydrogen sulfate. If so desired, additional ammonia may be added to unit F through conduit 3. The neutralized mixture then flows through conduit 4 to extraction unit C, wherein the lactam is extracted with an organic solvent supplied via conduit 5 and then discharged, as a solution of lactam in the solvent, through conduit 6 to a device for the recovery of lactam (not shown). The aqueous phase for extraction device C is next passed through conduit 7 to the apparatus for the decomposition of ammonium hydrogen sulfate D, this decomposition being effected by means of a reducing agent, e.g., natural gas, supplied through feed line 13.

The resulting gaseous mixture containing $NH_3$ and $SO_2$ is then passed through conduit 8 to absorption unit F, where the $NH_3$ and $SO_2$ are absorbed in water being supplied through conduit 17 and formed by condensation of water vapor in the gaseous mixture. The non-absorbed gas is discharged through conduit 18.

The $SO_2$ formed in neutralization unit B is delivered through conduit 9 to the installation E for the preparation of oleum or sulphuric acid, which installation is also fed with oxygen through conduit 15, and with water vapor through conduit 14, this water vapor being obtained in unit D by evaporation of the solution fed there into through conduit 7. If so required, liquid sulfur (to make additional $SO_3$ by oxidation) may also be fed through conduit 11. Any liquid components left in unit D are discharged from the system through conduit 12.

In FIG. 2, A again denotes a reactor for the rearrangement of cyclohexanone oxime to ε-caprolactam. Unit B is a neutralizer for the mixture of lactam and sulfuric acid, unit C is an extraction device for the extraction of lactam from the mixture of lactam and ammonium hydrogen sulfate formed in the partial neutralization, and unit D is a neutralizer for the neutralization of ammonium hydrogen sulfate. E represents an installation for evaporation and for the reducing decomposition of ammonium hydrogen sulfate, F denotes a sulfuric-acid or oleum plant, and G is an absorber for the absorption, in water, of the gas containing $NH_3$ and $SO_2$. Additional $NH_3$ may be fed to absorber G through conduit 5.

Figure 2:
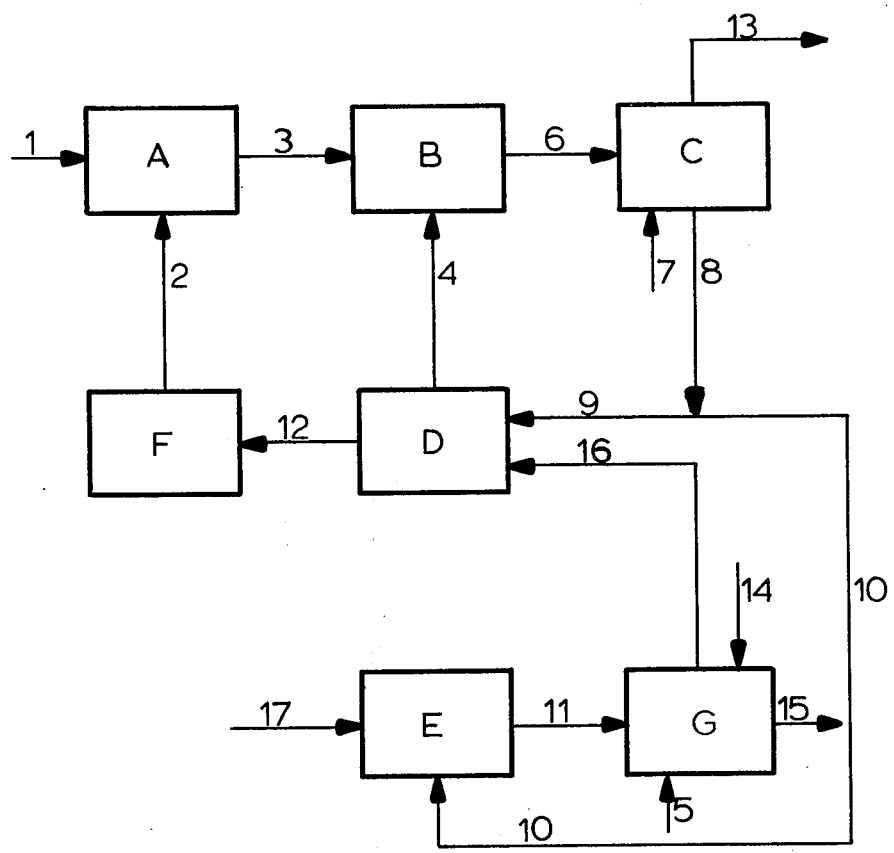
FIG. 2 schematically illustrates a second type of such installation.

In this FIG. 2, cyclohexanone oxime is fed through conduit 1 to the rearrangement reactor A, e.g., a mixing reactor provided with a stirrer or a vessel with a mixing cyclone, to which, through conduit 2 there is also fed sulfuric acid or oleum from the sulphuric acid or oleum plant F.

The reaction mixture then flows through conduit 3 to neutralizer B, which is fed through conduit 4 with a solution of ammonium sulfate from ammonium-hydrogen-sulfate neutralizer D.

The now partially-neutralized rearrangement reaction mixture next flows through conduit 6 to extraction device C, which, through conduit 7, is also fed with an organic extracting agent for the caprolactam, and in which sulfuric acid, ammonium sulfate and ammonium hydrogen sulfate are but poorly soluble. Suitable extraction agents include benzene, toluene, 1,2-dichloroethane, chloroform and 1,1,2,2-tetrachlorethane. The caprolactam dissolved in the extracting agent is then discharged from the system through conduit 13 and is passed to a device for the recovery of the lactam (not shown). The resulting aqueous solution of ammonium hydrogen sulfate is discharged through conduit 8, and in part passed through conduit 10 into decomposition device E, where, under reducing conditions, it is decomposed by means of natural gas, fed in through conduit 17, to form a gaseous mixture containing ammonia and sulfur dioxide. The remaining part of the ammonium hydrogen sulfate aqueous solution is cycled via conduit 9 to neutralizer D. This gaseous mixture is then passed through conduit 11 to absorber G, where the $NH_3$ and $SO_2$ are absorbed in water supplied through conduit 14 and water formed by condensation of the water vapor in the gaseous mixture. The non-absorbed gas is discharged through conduit 15.

In neutralizer D ammonium hydrogen sulfate is converted into ammonium sulfate by means of ammonium hydrogen sulfite formed in unit G and fed in through conduit 16.

A gaseous mixture containing mainly sulfur dioxide escapes from neutralizer D and is passed through conduit 12 to the sulfuric-acid or oleum plant F.

THE EXAMPLES

The following Examples will further illustrate specific modes of practice of the invention.

EXAMPLE I 36.9 kilomoles of $\epsilon$-caprolactam are prepared per hour in reactor unit A, according to the diagram of FIG. 1. The neutralization of the reaction mixture of lactam and sulfuric acid is carried out at atmospheric pressure and at a temperature of 40° C. The resulting lactam is extracted with chloroform.

The thermal decomposition of the ammonium hydrogen sulfate is carried out at 550° C. with addition of natural gas and air in the manner described in British Patent specification No. 1,014,945, the disclosure of which is incorporated herein by reference. This decomposition can be represented by the overall reaction equation:

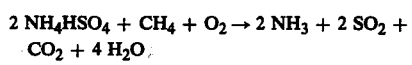

$$2\,NH_4HSO_4 + CH_4 + O_2 \rightarrow 2\,NH_3 + 2\,SO_2 + CO_2 + 4\,H_2O$$

The composition of the various product flows in kilomoles per hour is shown in the following Table 1. It is assumed that the yield of the $SO_2$ production in the above reaction is 100% and that of the $NH_3$ production 80%. The rearrangement of the oxime to the lactam is carried out with oleum. The $SO_3$ content in the oleum has been calculated as sulfuric acid.

TABLE 1

| Flow Line | Oxime | Lactam | $H_2SO_4$ | $(NH_4)_2SO_4$ | $H_2SO_3$ | $(NH_4)_2SO_3$ | $H_2O$ | $SO_2$ | $NH_3$ | $CO_2$ | $N_2$ | $CHCl_3$ | $CH_4$ |
|---|---|---|---|---|---|---|---|---|---|---|---|---|---|
| 1 | 36.9 | | | | | | | | | | | | |
| 2 | | 36.9 | 56 | | | | | | | | | | |
| 3 | | | | | | | | | 11.8 | | | | |
| 4 | | 36.9 | 26.5 | 29.5 | | | 551 | | | | | | |
| 5 | | | | | | | | | | | | 105 | |
| 6 | | 36.9 | | | | | | | | | | 105 | |
| 7 | | | 26.5 | 19.5 | | | 551 | | | | | | |
| 8 | | | | | | | 444 | 56 | 47.2 | 71 | 479 | | |
| 9 | | | | | | | 3 | 56 | | | | | |
| 10 | | | 56 | | | | | | | | | | |
| 13 | | | | | | | | | | | | | 71 |
| 16 | | | | | 26.5 | 29.5 | 498 | | | | | | |
| 17 | | | | | | | 143 | | | | | | |
| 18 | | | | | | | 33 | | | 71 | 479 | | |

In this Table, 2 moles of $NH_4HSO_4$ are equated with 1 mole of $(NH_4)_2SO_4$ + 1 mole of $H_2SO_4$ and 2 moles of $NH_4HSO_3$ are equated with 1 mole of $(NH_4)_2SO_3$ + 1 mole $H_2SO_3$.

EXAMPLE II 36.9 kilomoles of $\epsilon$-caprolactam are prepared per hour according to the diagram of FIG. 2. The neutralization of the mixture of lactam and sulfuric acid is effected at atmospheric pressure and 40° C. by means of ammonium sulfate obtained by reaction of ammonium hydrogen sulfate with ammonium hydrogen sulfite while sulfur dioxide is removed. The other process steps are carried out in the same way as in Example I. The composition of the various product flows in kilomoles per hour are shown in Table 2, where the same yields as in Example I have been assumed.

TABLE 3

| Flow Line | Oxime | Lactam | $H_2SO_4$ | $(NH_4)_2SO_4$ | $H_2SO_3$ | $(NH_4)_2SO_3$ | $H_2O$ | $SO_2$ | $NH_3$ | $CO_2$ | $N_2$ | $CHCl_3$ | $CH_4$ |
|---|---|---|---|---|---|---|---|---|---|---|---|---|---|
| 1 | 36.9 | | | | | | | | | | | | |
| 2 | | | 56 | | | | | | | | | | |
| 3 | | 36.9 | 56 | | | | | | | | | | |
| 4 | | | | 62.3 | | | 1164 | | | | | | |
| 5 | | | | | | | | | 11.8 | | | | |
| 6 | | 36.9 | 56 | 62.3 | | | 1164 | | | | | | |
| 7 | | | | | | | | | | | | 105 | |

TABLE 3-continued

| Flow Line | Oxime | Lactam | H$_2$SO$_4$ | (NH$_4$)$_2$SO$_4$ | H$_2$SO$_3$ | (NH$_4$)$_2$SO$_3$ | H$_2$O | SO$_2$ | NH$_3$ | CO$_2$ | N$_2$ | CHCl$_3$ | CH$_4$ |
|---|---|---|---|---|---|---|---|---|---|---|---|---|---|
| 8 | | | 56 | 62.3 | | | 1164 | | | | | | |
| 9 | | | 29.5 | 32.8 | | | 613 | | | | | | |
| 10 | | | 26.5 | 29.5 | | | 551 | | | | | | |
| 11 | | | | | | | 444 | 56 | 47.2 | 71 | 479 | | |
| 12 | | | | | | | 3 | 56 | | | | | |
| 13 | | 36.9 | | | | | | | | | | 105 | |
| 14 | | | | | | | 143 | | | | | | |
| 15 | | | | | | | 33 | | | 71 | 479 | | |
| 16 | | | | | 26.5 | 29.5 | 498 | | | | | | |
| 17 | | | | | | | | | | | | | 71 |

What is stated about NH$_4$HSO$_4$ and NH$_4$HSO$_3$ in Table 1 also applies herein.

What is claimed is:

1. In processes for the recovery of ε-caprolactam from reaction mixtures of ε-caprolactam and sulfuric acid, in which the sulfuric acid, after complete or partial neutralization with simultaneous formation of an ammonium salt, is separated from the lactam and an organic solvent is used to form a solution of lactam in the organic solvent from which the lactam is later recovered, the improvement consisting essentially in that said neutralized sulfuric acid is at least partially subjected to thermal decomposition to form a gaseous mixture containing ammonia and sulfur dioxide, contacting this gaseous mixture with water to form an aqueous solution containing ammonium sulfite and/or ammonium hydrogen sulfite, and to liberate an ammonia-free sulfur dioxide gas, thereafter using this aqueous sulfite solution, either as such or after being mixed with partially neutralized sulfuric acid that has not been subjected to the thermal decomposition, for the neutralization of the said reaction mixture of lactam and sulfuric acid, while the sulfur dioxide formed in this neutralization and/or said mixing is recycled to a synthesis plant wherein the sulfur dioxide is oxidised to sulfur trioxide.